United States Patent
Tokura et al.

(10) Patent No.: US 10,101,270 B2
(45) Date of Patent: Oct. 16, 2018

(54) SO3 ANALYSIS METHOD AND ANALYSIS DEVICE

(71) Applicants: NIPPON TELEGRAPH AND TELEPHONE CORPORATION, Tokyo (JP); MITSUBISHI HEAVY INDUSTRIES, LTD., Tokyo (JP)

(72) Inventors: Akio Tokura, Tokyo (JP); Osamu Tadanaga, Tokyo (JP); Kenji Muta, Tokyo (JP); Shuuji Fujii, Tokyo (JP); Yoichiro Tsumura, Tokyo (JP); Tatsuyuki Nishimiya, Tokyo (JP)

(73) Assignees: NIPPON TELEGRAPH AND TELEPHONE CORPORATION, Tokyo (JP); MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/560,752

(22) PCT Filed: Mar. 29, 2016

(86) PCT No.: PCT/JP2016/060006
§ 371 (c)(1),
(2) Date: Sep. 22, 2017

(87) PCT Pub. No.: WO2016/159985
PCT Pub. Date: Oct. 6, 2016

(65) Prior Publication Data
US 2018/0080866 A1 Mar. 22, 2018

(30) Foreign Application Priority Data
Mar. 31, 2015 (JP) ................................ 2015-071379

(51) Int. Cl.
*G01J 5/02* (2006.01)
*G01N 21/3504* (2014.01)
(Continued)

(52) U.S. Cl.
CPC ..... *G01N 21/3504* (2013.01); *G01N 33/0042* (2013.01); *G01N 2021/3595* (2013.01); *G01N 2201/06113* (2013.01)

(58) Field of Classification Search
CPC ............. G01N 33/0042; G01N 21/031; G01N 21/274; G01N 2021/3595; G01N 2201/128; G01N 21/3518; G01J 2003/1213
See application file for complete search history.

(56) References Cited

U.S. PATENT DOCUMENTS

| | | | |
|---|---|---|---|
| 5,340,987 A * | 8/1994 | Eckles | G01N 21/3504 250/343 |
| 8,247,775 B2 * | 8/2012 | Patel | G01N 33/0057 250/341.1 |

(Continued)

FOREIGN PATENT DOCUMENTS

| JP | 2000-304695 | 11/2000 |
|---|---|---|
| JP | 2001-188039 | 7/2001 |

(Continued)

OTHER PUBLICATIONS

International Search Report dated May 31, 2016 in International Application No. PCT/JP2016/060006, with English translation.

(Continued)

*Primary Examiner* — Kiho Kim
(74) *Attorney, Agent, or Firm* — Wenderoth, Lind & Ponack, L.L.P.

(57) ABSTRACT

To provide an $SO_3$ analysis device and analysis method capable of accurately and rapidly measuring the concentration of $SO_3$ in exhaust gas without pre-processing. The present invention is provided with a light source (11) for radiating laser light (2) to exhaust gas (1) including $SO_3$, $CO_2$, and $H_2O$, a photodetector (13) for receiving the laser light (2) radiated to the exhaust gas (1), a light source control (Continued)

unit (14a) of a control device (14) for controlling the wavelength of the laser light (2) radiated by the light source (11) so as to be 4.060 μm to 4.192 μm, and a concentration calculation unit (14b) of the control device (14) for calculating the SO3 concentration by infrared spectroscopy on the basis of the output from the photodetector (13) and a reference signal from the light source control unit (14a).

8 Claims, 17 Drawing Sheets

(51) Int. Cl.
*G01N 33/00* (2006.01)
*G01N 21/35* (2014.01)

(56) References Cited

U.S. PATENT DOCUMENTS

| 8,368,896 | B1 | 2/2013 | Li et al. | |
|---|---|---|---|---|
| 2012/0075632 | A1* | 3/2012 | Baasner | G01N 21/3504 356/437 |
| 2012/0235038 | A1* | 9/2012 | Nishikawa | G01J 5/0014 250/338.3 |
| 2015/0099274 | A1* | 4/2015 | Axelrod | C12M 41/34 435/39 |

FOREIGN PATENT DOCUMENTS

| JP | 2001-289783 | 10/2001 |
|---|---|---|
| JP | 2003-14633 | 1/2003 |
| JP | 2003-14634 | 1/2003 |
| JP | 2003-42950 | 2/2003 |
| JP | 3943853 | 7/2007 |
| JP | 2007-193034 | 8/2007 |
| JP | 2007-285823 | 11/2007 |
| JP | 2009-85872 | 4/2009 |
| JP | 2011-27699 | 2/2011 |
| JP | 2011-252843 | 12/2011 |
| JP | 2014-16313 | 1/2014 |

OTHER PUBLICATIONS

Written Opinion of the International Searching Authority dated May 31, 2016 in International Application No. PCT/JP2016/060006, with English translation.

Development of measurement technology of SOx in flue gas using infrared spectroscopy "-Evaluation of absorption characteristics of SOx at high temperature-", Central Research Institute of Electric Power Industry research report, thermal power generation, report No. H08006, Apr. 2009, with English Abstract.

O. Tadanaga, T. Yanagawa, Y. Nishida, H. Miyazawa, K. Magari, J. Asobe, H. Suzuki, "Efficient 3-μm difference frequency generation using direct-bonded quasi-phase-matched LiNbO3 ridge waveguides", 2006, Applied Physics Letters, vol. 88, No. 6, 061101-1-061101-3.

"Acid Dewpoint Temperature Measurement and its use in Estimating Sulfur Trioxide Concentration", p. 1-12, [online], [searched on Mar. 18, 2015], Internet <URL:http://www.ametekpi.com/download/Sulfur-Trioxide-Concentrations.pdf>.

Buzykin O.G. Spectroscopic Detection of Sulfer Oxiders in the Aircraft Wake, Journal of Russian Laser Research, USA, Springer, 2005, vol. 26, No. 5, p. 402-426.

Extended European Search Report dated Mar. 28, 2018 in European Application No. 16772776.7.

Rawlins et al., "Quantum cascade laser sensor for SO$_2$ and SO$_3$ for application to combustor exhaust streams", Applied Optics, 44(31):6635-6643 (2005).

Majkowski et al., "Infrared absorption coefficients of gaseous H$_2$SO$_4$ and SO$_3$", Applied Optics, 17(7):975-977 (1978).

* cited by examiner

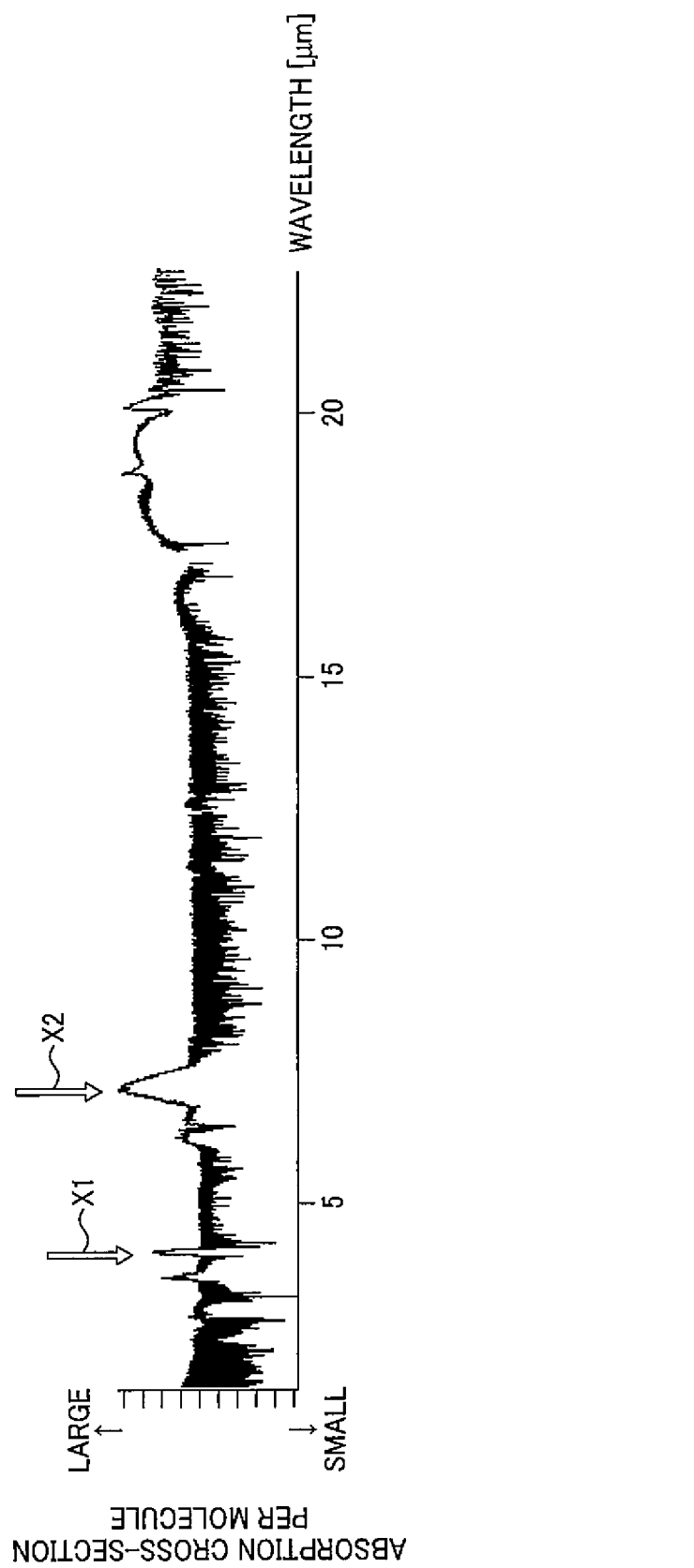

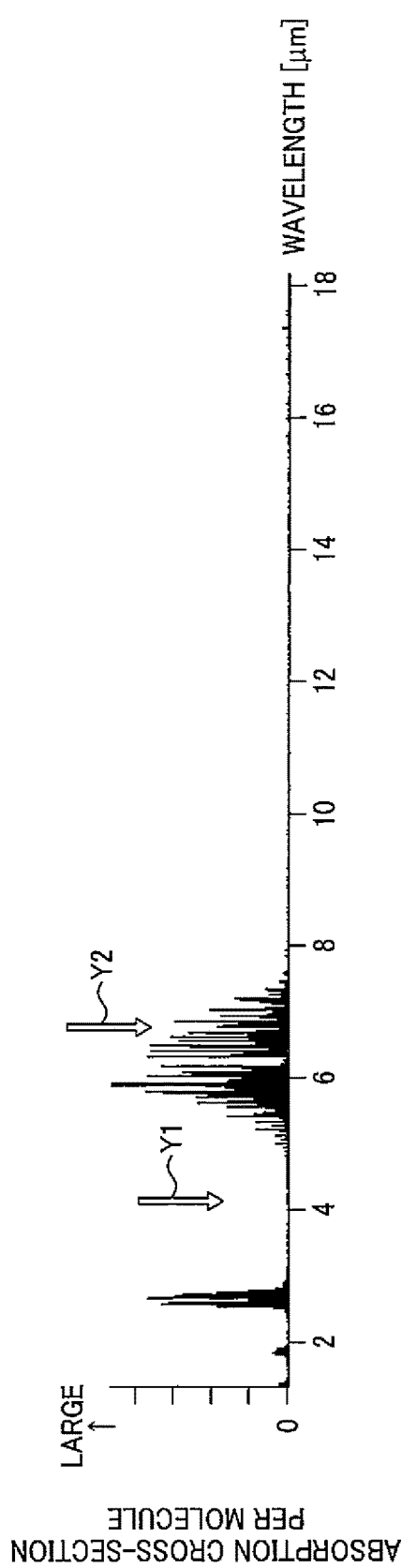

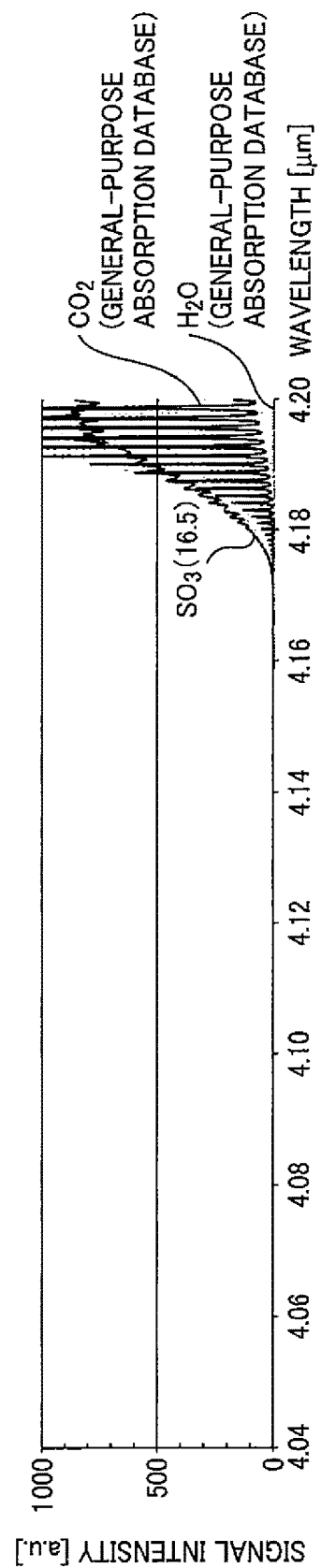

SO3 ANALYSIS METHOD AND ANALYSIS DEVICE

TECHNICAL FIELD

The present invention relates an $SO_3$ analysis method and analysis device.

BACKGROUND ART

Recently, the number of combustion plants using various heavy oils and coals as fuel has been increasing. These heavy oils and coals, containing a large amount of sulfur (hereinafter S), generate a large amount of sulfur dioxide (hereinafter $SO_2$) and sulfur trioxide (hereinafter $SO_3$) when they are simply combusted.

In particular, $SO_3$ becomes sulfuric acid (hereinafter $H_2SO_4$) when water vapor (hereinafter $H_2O$) exists in the same gas. For this reason, $SO_3$ is specified as a designated substance by Air Pollution Control Law (in Japan) as one of causative substances of acid rain.

In combustion plants, a neutralizing agent such as ammonia (hereinafter $NH_3$) is added to flue gas which is discharged from the plant to create solid neutralization products, which is removed with a dust arrester, so that the concentration of $SO_3$ in the flue gas is lower than or equal to a specified value. However, since it has been difficult until now to continuously measure $SO_3$, the injection amount of $NH_3$ could not be optimally controlled. When the injection amount of $NH_3$ is too large, it creates a large amount of ammonium sulfate, which clogs the dust arrester. In contrast, when the injection amount of $NH_3$ is too small, it causes corrosion by $H_2SO_4$. Hence, the plant could be continuously operated only for a short period.

Measurement analyses of $SO_3$ which have been conventionally conducted include: a method in which the gas is sampled using wet sampling, and all the amount is retrieved as $H_2SO_4$, which is then subjected to chemical analysis (including also a liquid chromatography analysis); and a method in which gas sampling is performed, and after removing dust, optical analysis is performed with a long-wavelength mid-infrared (around 7 μm) spectroscopy such as a Fourier transform infrared spectroscopy (FT-IR).

In addition, in recent years, a gas analysis device capable of continuously analyzing $SO_3$ using a long-wavelength mid-infrared quantum cascade laser (hereinafter QCL) after gas sampling has been developed, studied, and sold in the market (for example, refer to Non-Patent Document 1 below).

PRIOR ART DOCUMENT

Patent Document

Patent Document 1: Japanese Patent No. 3943853

Non-Patent Document

Non-Patent Document 1: Development of measurement technology of SOx in flue gas using infrared laser spectroscopy "—Evaluation of absorption characteristics of SOx at high temperature—", Central Research Institute of Electric Power Industry research report, thermal power generation, report number H08006, April 2009

Non-Patent Document 2: O. Tadanaga, T. Yanagawa, Y. Nishida, H. Miyazawa, K. Magari, M. Asobe, H. Suzuki, "Efficient 3-μm difference frequency generation using direct-bonded quasi-phase-matched LiNbO3 ridge waveguides", 2006, APPLIED PHYSICS LETTERS, Vol. 88, No. 6, 061101-1-061101-3.

Non-Patent Document 3: "Acid Dewpoint Temperature Measurement and its use in Estimating Sulfur Trioxide Concentration", p. 1-12, [online], [searched on Mar. 18, 2015], Internet <URL:http://www.ametekpi.com/download/Sulfur-Trioxide-Concentrations.pdf>

SUMMARY OF THE INVENTION

Problems to be Solved by the Invention

However, even the gas analysis device described in Non-Patent Document 1 requires pretreatment such as removing dust and injecting dry air, nitrogen (hereinafter $N_2$), or the like for $H_2O$ dilution, and in addition, the analysis is performed under a reduced pressure to reduce interference of coexisting gases. Thus, this gas analysis device has problems of requiring much cost and time. In addition, since the gas analysis device involves sampling and the pretreatment step, it is difficult to measure the concentration of $SO_3$ in real time.

For analysis with a QCL utilizing long-wavelength mid-infrared light (7 μm) and FT-IR analysis, only a material having a high deliquescent property such as $CaF_2$ or $MgF_2$ can be used for window material, which makes it impossible to directly measure combustion flue gas containing a large amount of $H_2O$. In addition, since an absorption line of $SO_3$ is close to an absorption line of $H_2O$ in a 7 μm band, it is difficult to measure while avoiding the interference.

In view of the above, the present invention is made to solve the problems described above, and an object thereof is to provide an $SO_3$ analysis method and analysis device capable of directly measuring the concentration of $SO_3$ in flue gas without pretreatment.

Means for Solving the Problems

To solve the above problems, an $SO_3$ analysis device according to a first aspect of the invention comprises: light emission means for emitting laser light to gas containing $SO_3$, $CO_2$, and $H_2O$; light reception means for receiving the laser light that has been emitted to the gas and has passed through the gas; wavelength control means for performing control such that a wavelength of the laser light emitted by the light emission means is at an absorption wavelength of $SO_3$ in a 4.060 to 4.182 μm band; and $SO_3$ concentration calculation means for calculating a concentration of $SO_3$ by means of infrared spectroscopy based on an output from the light reception means and a reference signal from the wavelength control means.

To solve the above problems, an $SO_3$ analysis device according to a second aspect of the invention is the $SO_3$ analysis device according to the first aspect of the invention, wherein the wavelength control means performs control such that the wavelength of the laser light is 4.093 to 4.098 μm, 4.1045 to 4.1065 μm, 4.110 to 4.115 μm, 4.117 to 4.126 μm, or 4.131 to 4.132 μm.

To solve the above problems, an $SO_3$ analysis device according to a third aspect of the invention is the $SO_3$ analysis device according to the first or second aspect of the invention, wherein the light emission means includes non-linear optical crystal, generates, by means of difference frequency generation using inputs of laser light with a wavelength of $\lambda_1$ and laser light of a wavelength of $\lambda_2$, laser light with a wavelength of $\lambda_3$ satisfying $1/\lambda_3=1/\lambda_1-1/\lambda_2$, and outputs the laser light with the wavelength of $\lambda_3$.

To solve the above problems, an $SO_3$ analysis device according to a fourth aspect of the invention is the $SO_3$ analysis device according to any one of the first to third aspects of the invention, further comprising temperature measurement means for measuring a temperature of the gas, wherein the $SO_3$ concentration calculation means calculates the concentration of $SO_3$ by means of the infrared spectroscopy using also the temperature of the gas measured by the temperature measurement means.

To solve the above problems, an $SO_3$ analysis device according to a fifth aspect of the invention is the $SO_3$ analysis device according to any one of the first to fourth aspects of the invention, further comprising pressure measurement means for measuring a pressure of the gas, wherein the $SO_3$ concentration calculation means calculates the concentration of $SO_3$ by means of the infrared spectroscopy using also the pressure of the gas measured by the pressure measurement means.

To solve the above problems, an $SO_3$ analysis device according to a sixth aspect of the invention is the $SO_3$ analysis device according to any one of the first to fifth aspects of the invention, further comprising: $H_2O$ concentration measurement means for measuring a concentration of $H_2O$ in the gas; and $H_2SO_4$ concentration calculation means for calculating a concentration of $H_2SO_4$ by means of equilibrium calculation using the concentration of $SO_3$ calculated by the $SO_3$ concentration calculation means and the concentration of $H_2O$ measured by the $H_2O$ concentration measurement means.

To solve the above problems, an $SO_3$ analysis device according to a seventh aspect of the invention is the $SO_3$ analysis device according to any one of the first to sixth aspects of the invention, further comprising sampling means for sampling the gas, wherein the light emission means emits the laser light to the gas sampled by the sampling means.

To solve the above problems, an $SO_3$ analysis device according to an eighth aspect of the invention is the $SO_3$ analysis device according to the seventh aspect of the invention, further comprising heating means for heating the gas sampled by the sampling means.

To solve the above problems, an $SO_3$ analysis method according to a ninth aspect of the invention comprises: emitting, by light emission means, laser light to gas containing $SO_3$, $CO_2$, and $H_2O$, the laser light having a wavelength controlled at 4.060 to 4.182 μm by wavelength control means; receiving, by light reception means, the laser light emitted to the gas; and calculating a concentration of $SO_3$ by means of infrared spectroscopy based on an output from the light reception means and a reference signal from the wavelength control means.

Effect of the Invention

The present invention makes it possible to measure in-situ (directly measure) the concentration of $SO_3$, which was conventionally impossible, and eliminates the need of a large-scale modification work such as attaching measurement windows to the equipment of a combustion plant. Accordingly, even in the case where the gas is sampled for sampling measurement, it is possible to measure the concentration of $SO_3$ in the flue gas accurately and promptly without pretreatment.

BRIEF DESCRIPTION OF THE DRAWINGS

FIG. 1A is an explanatory diagram illustrating an absorption spectrum of $SO_3$ in an $SO_3$ analysis method according to a main embodiment of the present invention.

FIG. 1B is an explanatory diagram illustrating an absorption spectrum of $H_2O$ in the $SO_3$ analysis method according to the main embodiment of the present invention.

FIG. 3C is a graph illustrating influence evaluation of coexisting gases, which is performed to check the effect of the $SO_3$ analysis method, and in which an FT-IR measurement test result in the wavelength range of 4.040 to 4.200 μm for the case where the concentration of $SO_3$ is 16.5 ppm as well as the absorption spectrum database are used.

MODE FOR CARRYING OUT THE INVENTION

Figure 2A:
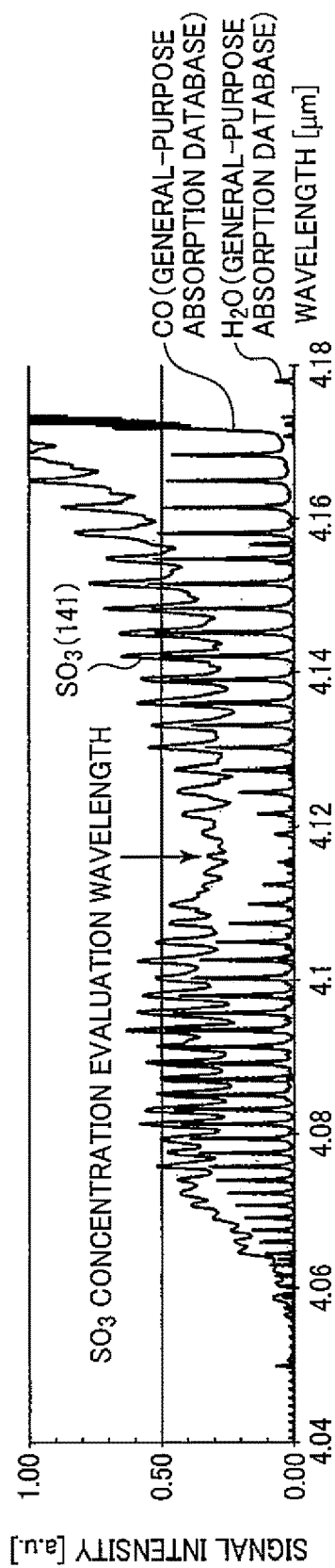
FIG. 2A is a graph illustrating influence evaluation of coexisting gases, which is performed to check the effect of the $SO_3$ analysis method, and in which an FT-IR measurement test result in a wavelength range of 4.040 to 4.180 μm for the case where the concentration of $SO_3$ is 141 ppm as well as an absorption spectrum database are used.
Figure 2B:
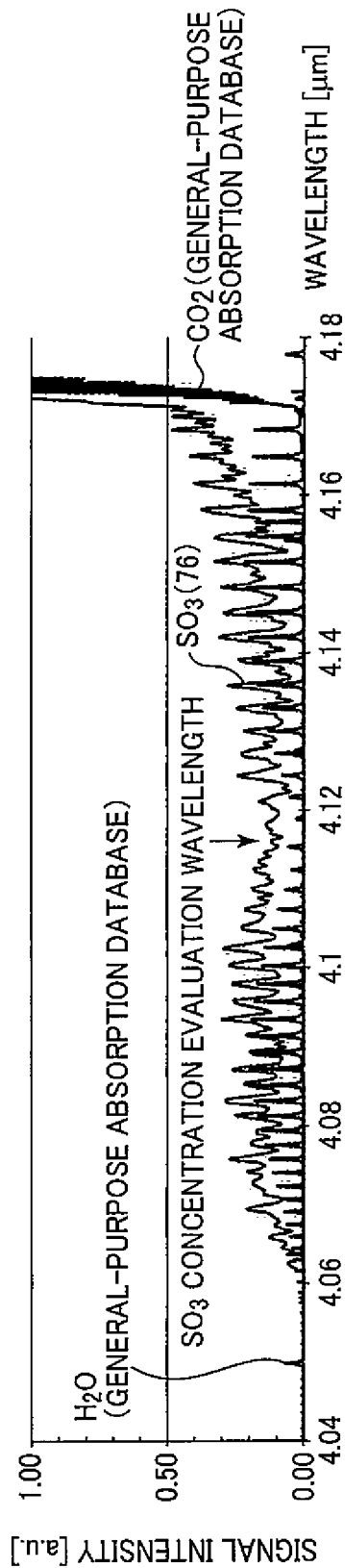
FIG. 2B is a graph illustrating influence evaluation of coexisting gases, which is performed to check the effect of the $SO_3$ analysis method, and in which an FT-IR measurement test result in the wavelength range of 4.040 to 4.180 μm for the case where the concentration of $SO_3$ is 76 ppm as well as the absorption spectrum database are used.
Figure 2C:
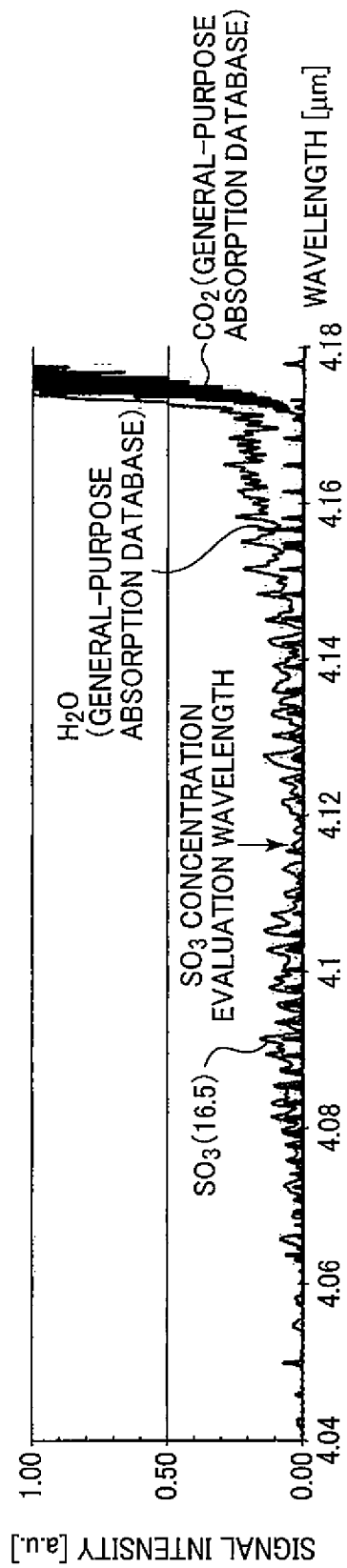
FIG. 2C is a graph illustrating influence evaluation of coexisting gases, which is performed to check the effect of the $SO_3$ analysis method, and in which an FT-IR measurement test result in the wavelength range of 4.040 to 4.180 μm for the case where the concentration of $SO_3$ is 16.5 ppm as well as the absorption spectrum database are used.
Figure 3A:
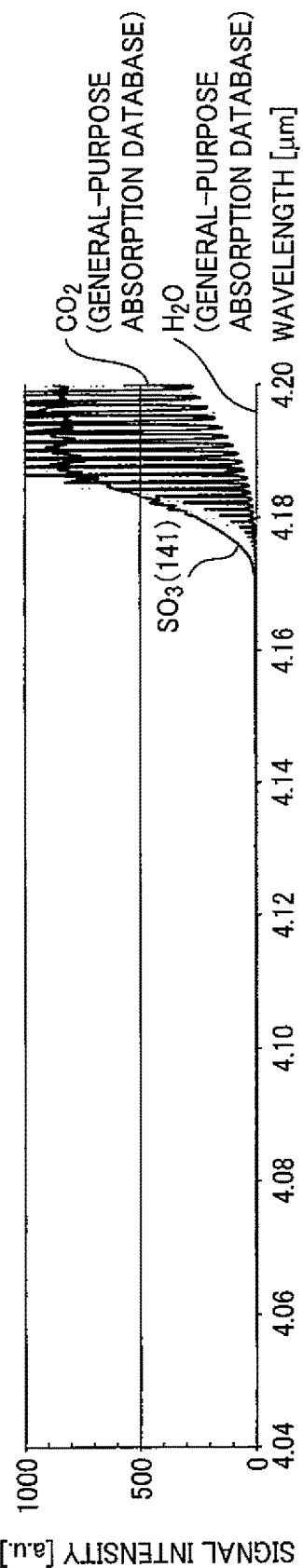
FIG. 3A is a graph illustrating influence evaluation of coexisting gases, which is performed to check the effect of the $SO_3$ analysis method, and in which an FT-IR measurement test result in a wavelength range of 4.040 to 4.200 μm for the case where the concentration of $SO_3$ is 141 ppm as well as the absorption spectrum database are used.
Figure 3B:
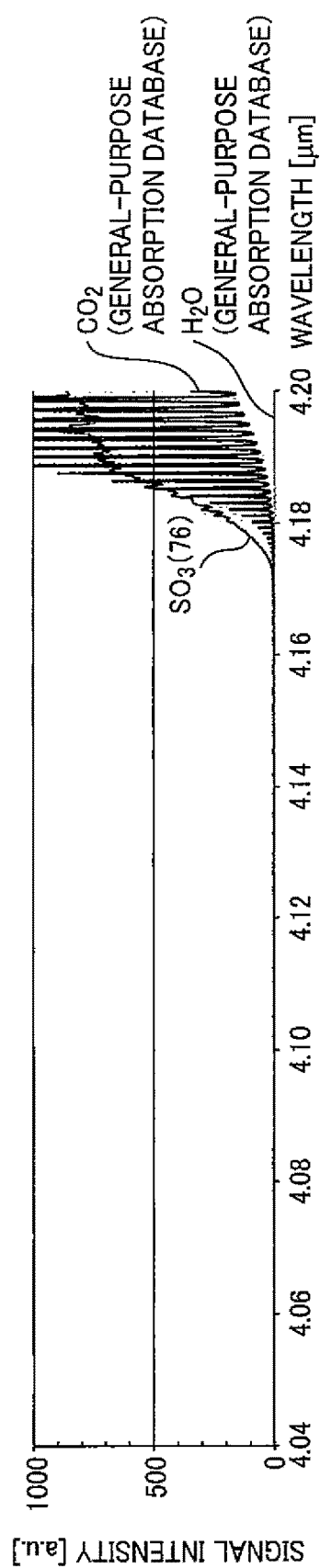
FIG. 3B is a graph illustrating influence evaluation of coexisting gases, which is performed to check the effect of the $SO_3$ analysis method, and in which an FT-IR measurement test result in the wavelength range of 4.040 to 4.200 μm for the case where the concentration of $SO_3$ is 76 ppm as well as the absorption spectrum database are used.

Descriptions will be provided for a main embodiment of an $SO_3$ analysis method and analysis device according to the present invention based on the drawings. However, the present invention is not limited only to the following main embodiment described based on the drawings.

[Main Embodiment]

First, the inventors did a literature search on the information about the $SO_3$ spectrum in the mid-infrared region (2 to 20 μm). As a result, as illustrated in FIG. 1A, it was found that in addition to the spectrum around 7 μm (arrow X2 in FIG. 1A) used for conventional optical measurement, there is a strong absorption spectrum around 4.1 μm (arrow X1 in FIG. 1A). It is thought that using this wavelength range makes it possible to avoid the above problem that the concentration of $SO_3$ in gas containing a large amount of $H_2O$ cannot be measured due to the deliquescent property of measurement windows, and enables sapphire having no deliquescent property and high strength to be used for the window plates, thereby allowing for in-situ measurement of the gas. Similarly, a literature search on the information about the $H_2O$ spectrum in the mid-infrared region (2 to 20 μm) showed, as illustrated in FIG. 1B, that there is a strong spectrum around 7 μm (arrow Y2 in FIG. 1B) but that there is no strong absorption spectrum around 4.1 μm (arrow Y1 in FIG. 1B). Hence it is thought that the coexistence of $H_2O$, which is a problem particularly in ordinary optical measurement, does not affect the measurement using the wavelength range around 4.1 μm.

However, no detailed information about this wavelength range was available on documents such as academic papers, and the accuracy of the information in FIGS. 1A and 1B had not been confirmed. For this reason, since it was not known which absorption line was suitable to measure for gas concentration analysis, $SO_3$ analysis method and analysis device based on the gas absorption spectroscopy using 4 μm range was unable to be built, no matter how those skilled in the art had designed or devised within the conventional technical scope.

In this respect, to know the absorption spectrum in this vicinity, an experiment was conducted by measuring with an FT-IR that was capable of measuring a wide wavelength range although its wavelength resolution was as low as 0.5 $cm^{-1}$. The conditions were as follows: the optical path length was 5.1 m, the gas temperature was about 200° C., the gas pressure was about 1 atmospheric pressure, and the concentration of $SO_3$ was changed to 141, 76, and 16.5 ppm. As a coexisting gas, $CO_2$ at a concentration of 10% or less was added. At the same time, the influence of $CO_2$ was simultaneously evaluated using a general absorption spectrum database (data of $SO_3$ are not included). Although $H_2O$ was not added this time, the influence of adding $H_2O$ at a concentration of 10% was also evaluated using the absorption spectrum database. The results are illustrated in FIGS. 2A to 2C and FIGS. 3A to 3C. As is apparent from FIGS. 2A to 2C and FIGS. 3A to 3C, the peak positions in the region where the envelope shape of the FT-IR and the envelope shape of the $CO_2$ spectrum from the absorption spectrum database generally correspond to each other generally correspond to those of the $CO_2$ calculated using the absorption spectrum database. Hence, it turned out that these peaks were not $SO_3$ peaks. On the other hand, the region where there is a difference from the envelope shape of the $CO_2$ spectrum is the wavelength range of the $SO_3$ spectrum. As illustrated in FIGS. 2A to 2C and FIGS. 3A to 3C, it was shown from the comparison to the envelope shape of the $CO_2$ spectrum that the wavelength range of the $SO_3$ spectrum starts from 4.060 μm and continues to 4.182 μm. It has also been shown that the interference with $H_2O$ is not so large as to make the $SO_3$ concentration measurement extremely difficult.

Figure 4:
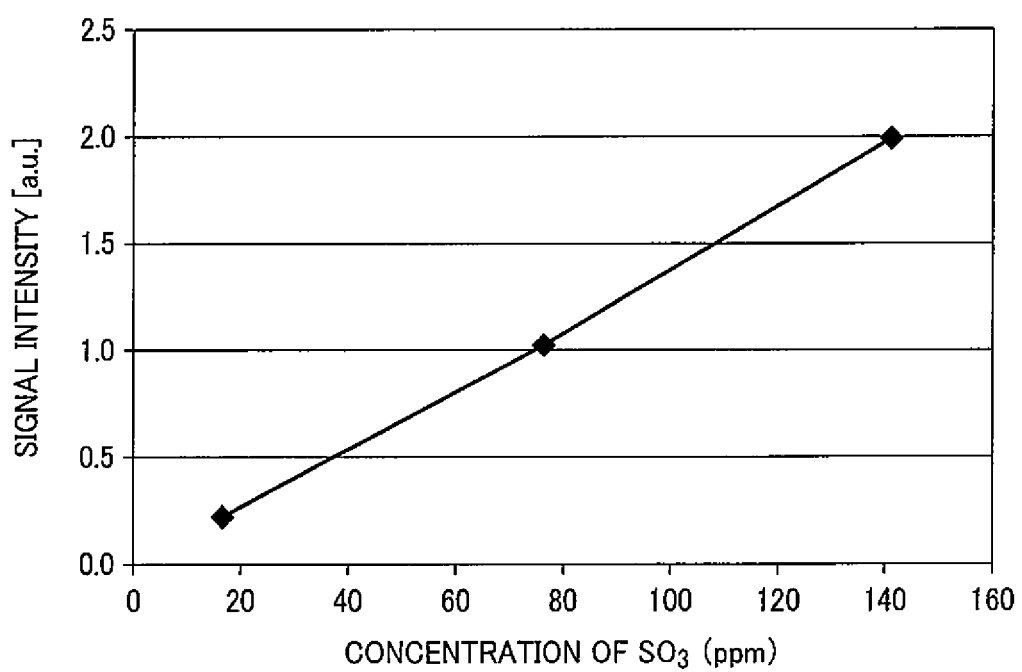
FIG. 4 is a graph illustrating the relationship between the aforesaid concentrations of $SO_3$ and the signal intensities around the wavelength of 4.18 μm.

Here, FIG. 4 illustrates a result of comparison between the spectral intensity and the concentration of $SO_3$ in a wavelength range around 4.18 μm where there is no influence of $CO_2$. As illustrated in FIG. 4, it was shown that the spectral intensity and the concentration of $SO_3$ clearly correlate with each other in the wavelength range where there is no influence of $CO_2$.

Figure 5:
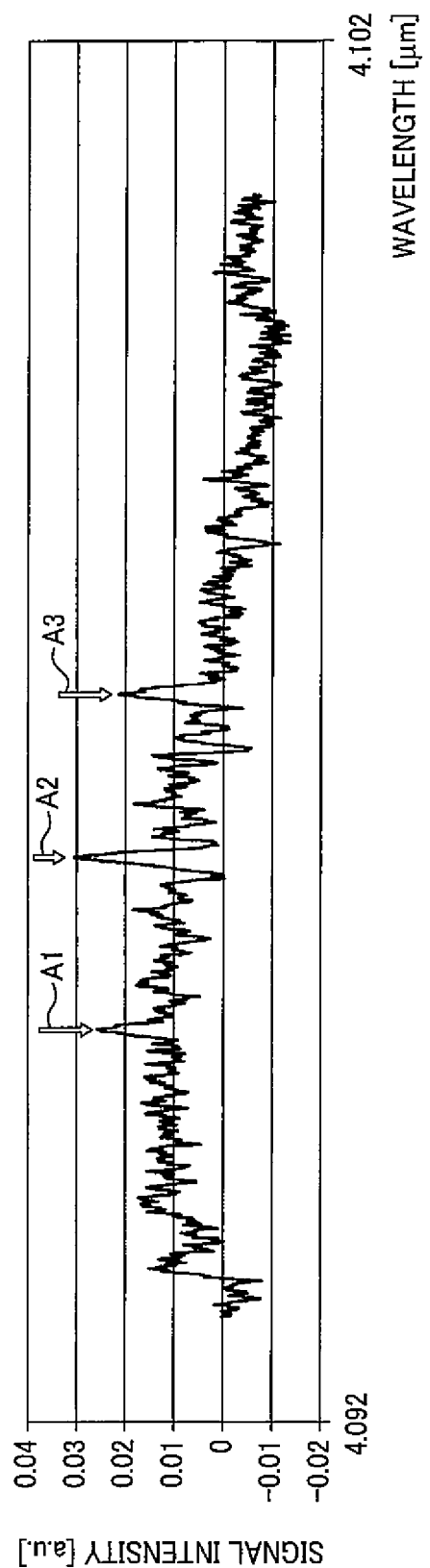
FIG. 5 is a graph illustrating an example of $SO_3$ spectrum.

Then, using a light source based on difference frequency generation, which will be described in detail later, the gas with an $SO_3$ concentration of about 150 ppm (all the pressure is balanced to be constant using an inert gas having no strong absorption in the measurement range), a temperature of about 300° C., and a pressure of 1 atmospheric pressure, was measured in the range of 4.040 to 4.200 μm at a high wavelength resolution. Here, FIG. 5 illustrates the result of measuring the $SO_3$ absorption spectrum in the wavelength range of 4.093 to 4.101 μm. As illustrated in FIG. 5, it was shown that peaks resulting from absorption of $SO_3$ exist in the three regions of A1, A2, and A3 of the signal intensity of the absorption measurement. In addition, it was shown that peaks resulting from absorption of $SO_3$ exist also in the wavelength ranges of 4.1045 to 4.1065 μm, 4.110 to 4.115 μm, 4.117 to 4.126 μm, and 4.131 to 4.132 μm of the signal intensity of the absorption measurement, in the same way as in the wavelength range of 4.093 to 4.101 μm. In other words, it was shown that many peaks in the $SO_3$ spectrum exist in the wavelength range of 4.060 to 4.182 μm. Therefore, it was discovered for the first time that by using the aforesaid light source and using the aforesaid $SO_3$ absorption spectrum obtained by the measurement described above at the high wavelength resolution, it is possible to measure in-situ the concentration of $SO_3$ in gas. In addition, from the evaluation using the above absorption spectrum database, it was discovered that the absorption peaks of $SO_3$ also exist in regions that are hardly affected by the absorption peaks of $CO_2$ and $H_2O$. Thus, it was discovered for the first time that the in-situ measurement of the concentration of $SO_3$ in gas is possible even if the gas to be measured contains $CO_2$ and $H_2O$ together with $SO_3$.

Next, descriptions will be provided based on the drawings for an $SO_3$ analysis method and analysis device according to the present invention. However, the present invention is not limited only to the following examples described based on the drawings.

FIRST EXAMPLE

Descriptions will be provided for an $SO_3$ analysis device according to a first example of the present invention using FIGS. 6 to 9.

Figure 6:
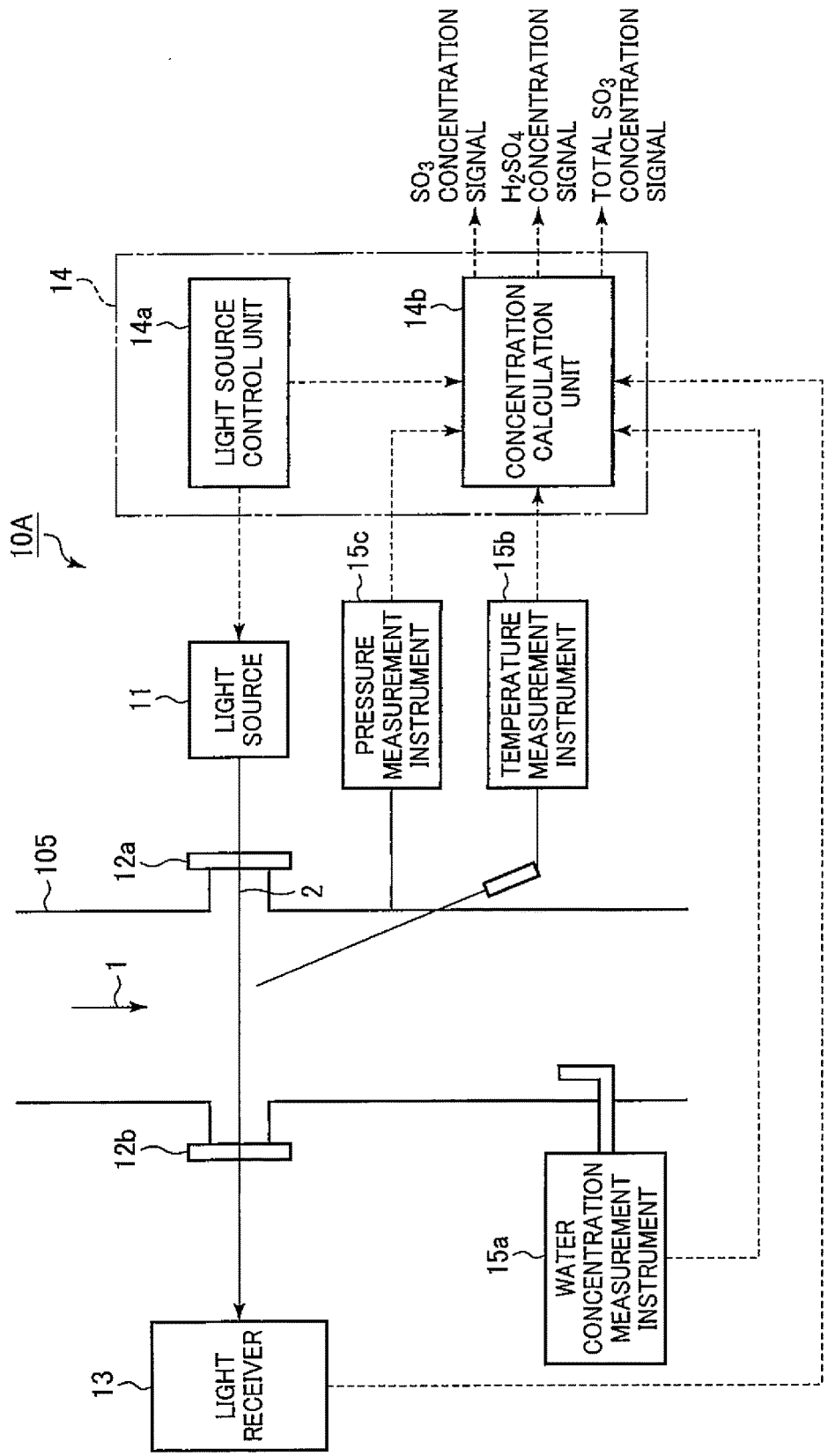
FIG. 6 is a schematic configuration diagram of an $SO_3$ analysis device according to a first example of the present invention.

As illustrated in FIG. 6, an $SO_3$ analysis device 10A according to this example includes a light source 11, windows 12a and 12b, a light receiver 13, a control device 14, a water concentration measurement instrument 15a, a temperature measurement instrument 15b, a pressure measurement instrument 15c. The control device 14 includes a light source control unit 14a and a concentration calculation unit 14b. The concentration calculation unit 14b calculates and outputs the concentration of $SO_3$, the concentration of $H_2SO_4$, and the total concentration of $SO_3$ based on a light reception signal from the light receiver 13, a water concentration signal from the water concentration measurement instrument 15a, a temperature signal from the temperature measurement instrument 15b, a pressure signal from the pressure measurement instrument 15c, and a light source control reference signal from the light source control unit 14a.

The windows 12a and 12b are arranged to face each other at a flue 105 through which flue gas 1 flows, and can be passed through by laser light 2. It is preferable that the windows 12a and 12b are made of, for example, sapphire. This is because that sapphire does not have a deliquescent property and eliminates the need of maintenance such as replacing the windows.

The light receiver 13 receives the laser light 2 emitted by the light source 11 and having passed through the window 12a, the flue 105, and the window 12b. A light intensity signal (light reception signal) obtained by the light receiver 13 is outputted to the concentration calculation unit 14b of the control device 14.

The water concentration measurement instrument 15a is disposed so as to measure the concentration of water in the flue gas 1 at generally the same position as the laser measurement position in the flue 105, and capable of measuring the concentration of water in the flue gas 1 flowing through the flue 105. The concentration of water in the flue gas 1, which is a measurement result of measuring with the water concentration measurement instrument 15a, is converted into the water concentration signal, which is outputted to the concentration calculation unit 14b of the control device 14.

The temperature measurement instrument 15b is disposed so as to measure the temperature at generally the same position as the laser measurement position in the flue 105, and capable of measuring the temperature of the flue gas 1 flowing through the flue 105. The temperature of the flue gas 1, which is a measurement result of measuring with the temperature measurement instrument 15b, is converted into the temperature signal, which is outputted to the concentration calculation unit 14b of the control device 14.

The pressure measurement instrument 15c is disposed so as to measure the pressure at generally the same position as the laser measurement position in the flue 105, and capable of measuring the pressure of the flue gas 1 flowing through the flue 105. The pressure of the flue gas 1, which is a measurement result of measuring with the pressure measurement instrument 15c, is converted into the pressure signal, which is outputted to the concentration calculation unit 14b of the control device 14.

The light source control unit 14a transmits a light source control signal to the light source 11 to control the wavelength of the laser light 2 emitted by the light source 11, and transmits a light source control reference signal to the concentration calculation unit 14b. The light source control reference signal is a signal having the wavelength information on the laser light emitted by the light source 11 based on the light source control signal.

The concentration calculation unit 14b calculates the concentration of $SO_3$ and outputs a signal on this concentration of $SO_3$. The concentration calculation unit 14b calculates the concentration of $SO_3$ by means of infrared spectroscopy based on the light source control reference signal transmitted from the light source control unit 14a, the light reception signal obtained by the light receiver 13, the water concentration signal transmitted from the water concentration measurement instrument 15a, the temperature signal transmitted from the temperature measurement instrument 15b, and the pressure signal transmitted from the pressure measurement instrument 15c. However, when the concentration of water, the temperature of the gas, and the pressure of the gas are already known, and are generally constant, the concentration of $SO_3$ can be calculated without always referring to these signals.

Figure 7:
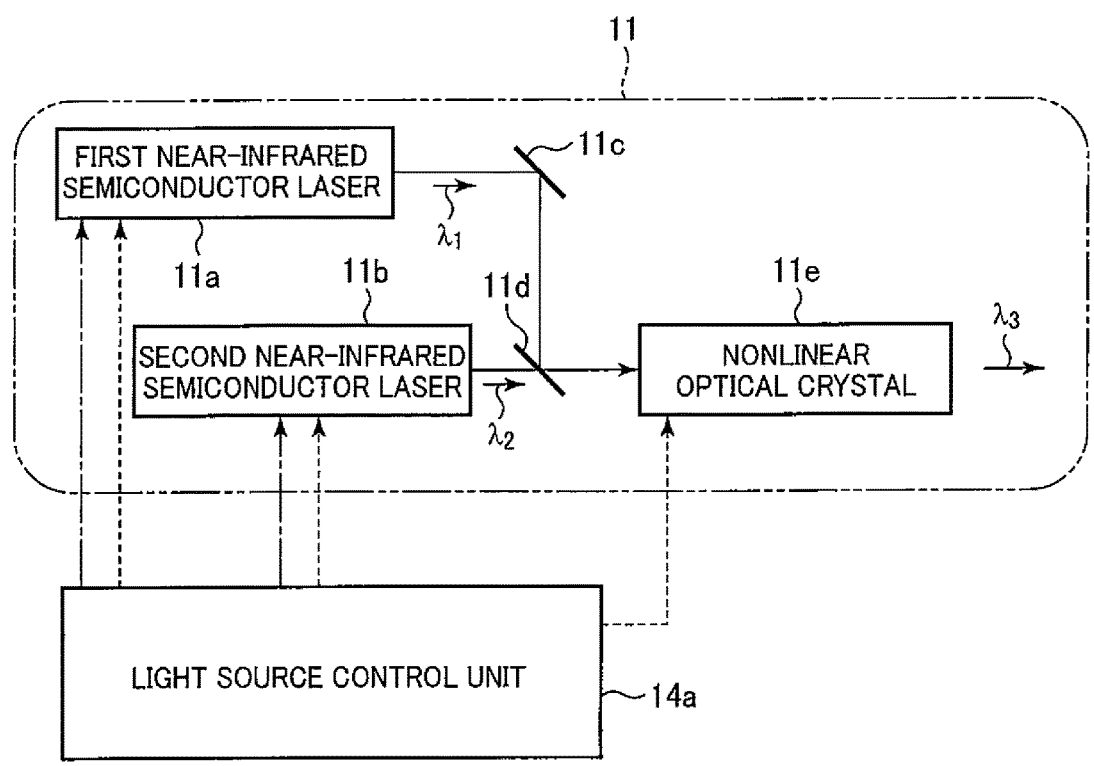
FIG. 7 is a diagram illustrating an example of a light source included in the $SO_3$ analysis device.

Here, descriptions will be provided for an example of the light source 11 and the light source control unit 14a using FIG. 7. Note that, in FIG. 7, dotted lines and dashed dotted lines outputted from the light source control unit 14a to two near-infrared semiconductor lasers 11a and 11b represent temperature control signal lines and electric current control lines, respectively. The dotted line outputted from the light source control unit 14a to a nonlinear optical crystal 11e represents a temperature control signal line.

As illustrated in FIG. 7, the light source 11 includes the two near-infrared semiconductor lasers 11a and 11b having different wavelengths (hereinafter referred to as NIR-LDs, wavelength $\lambda_1 < \lambda_2$), a mirror (reflection mirror) 11c, a multiplexer 11d, and the nonlinear optical crystal 11e. In the light source 11 thus configured, laser light having the wavelength $\lambda_1$ generated from the first (one) NIR-LD 11a is inputted into the nonlinear optical crystal 11e via the mirror 11c and the multiplexer 11d, and at the same time, laser light having the wavelength $\lambda_2$ ($\lambda_2 > \lambda_1$) generated from the second (the other) NIR-LD 11b is inputted into the nonlinear optical crystal via the multiplexer 11d. As a result, the light source 11 emits laser light having a short-wavelength mid-infrared wavelength $\lambda_3$ ($1/\lambda_3 = 1/\lambda_1 - 1/\lambda_2$), which is the difference-frequency light. This difference frequency generation is based on the second order nonlinear optical effect and occurs in a second order nonlinear optical crystal. As second order nonlinear optical crystals, lithium niobate (LN), lithium tantalate (LT), and potassium titanyl phosphate (KTP) which have large nonlinear constants are well known.

In addition, to utilize the nonlinear constant efficiently, the phases of the wavelengths $\lambda_1$, $\lambda_2$, and $\lambda_3$ of the incident and outgoing laser lights need to be matched, and the angle matching method or the quasi phase matching method are used for it. For example, in Non-Patent Document 2, LN is used as a nonlinear optical crystal, a periodic polarization reversal structure is adopted to achieve the quasi phase matching, and a waveguiding structure is further adopted to generate a mid-infrared light in a 3 µm band with high efficiency. Although in Non-Patent Document 2, a light of a 3 µm band is generated, for example, it is possible to generate a short-wavelength mid-infrared light with a desired wavelength $\lambda_3$ in a 2 to 5 µm range, by appropriately selecting the wavelength $\lambda_1$ and the wavelength $\lambda_2$, which are in the near-infrared range.

In this case, the stability/robustness of the device is guaranteed by using NIR-LD light sources, which have been used for many applications for communication or the like, for the wavelength conversion. In addition, in a QCL that oscillates and generates a long-wavelength mid-infrared light, since the wavelength line width of the generated laser light is wide, the measurement tends to be affected by coexisting gases. On the other hand, since in this example, the NIR-LDs, the wavelength line widths of which are extremely narrow, are used as origins, the wavelength line width of the generated short-wavelength mid-infrared laser light is as narrow as the NIR-LDs, and this example has a characteristic of being hardly affected by coexisting gases.

Note that although the incident lights from the two NIR-LDs 11a and 11b enter the nonlinear optical crystal 11e through the spatial optical system in FIG. 7, optical fibers can be used for the incidence.

The light source 11 is controlled by the light source control unit 14a, which performs temperature control for the two NIR-LDs 11*a* and 11*b* and the nonlinear optical crystal 11*e*, and electric current control for the two NIR-LDs 11*a* and 11*b*. Appropriate setting of the temperature allows for precise control of the oscillation wavelengths at the NIR-LDs 11*a* and 11*b*, and precise control of the efficiency of the difference frequency generation at the nonlinear optical crystal 11*e*.

Further, in this example, utilizing short-wavelength mid-infrared (around 4.1 µm) for the measurement wavelength allows sapphire window plates having high strength/corrosion resistance to be utilized for the windows 12*a* and 12*b*. On the other hand, since, in a QCL utilizing long-wavelength mid-infrared (7 to 8 µm), only $CaF_2$, $MgF_2$, or the like having a high deliquescent property can be used for window material, it is impossible to directly measure combustion flue gas containing a large amount of $H_2O$.

In the above example, when the temperature of the flue gas 1 is higher than the acid dew point, $SO_3$ and $H_2SO_4$ exist in the state of gas. Hence, the total concentration of $SO_3$ (the sum total of the concentration of $SO_3$ and the concentration of $H_2SO_4$) was first measured using a wet analysis of hand analysis. As a result, it was confirmed that the total concentration of $SO_3$ was constantly 150 ppm. The temperature of the flue gas was also measured with the temperature measurement instrument and was stably 290° C.

Next, the gas properties of the flue gas 1 was changed, thereby changing only the concentration of $H_2O$. At that time, the concentration of $H_2O$ in the flue gas 1 was measured with the water concentration measurement instrument, and it was confirmed that the concentrations of $H_2O$ were stable in the four conditions, 0%, 1.12%, 3.49%, and 10%.

Figure 8:
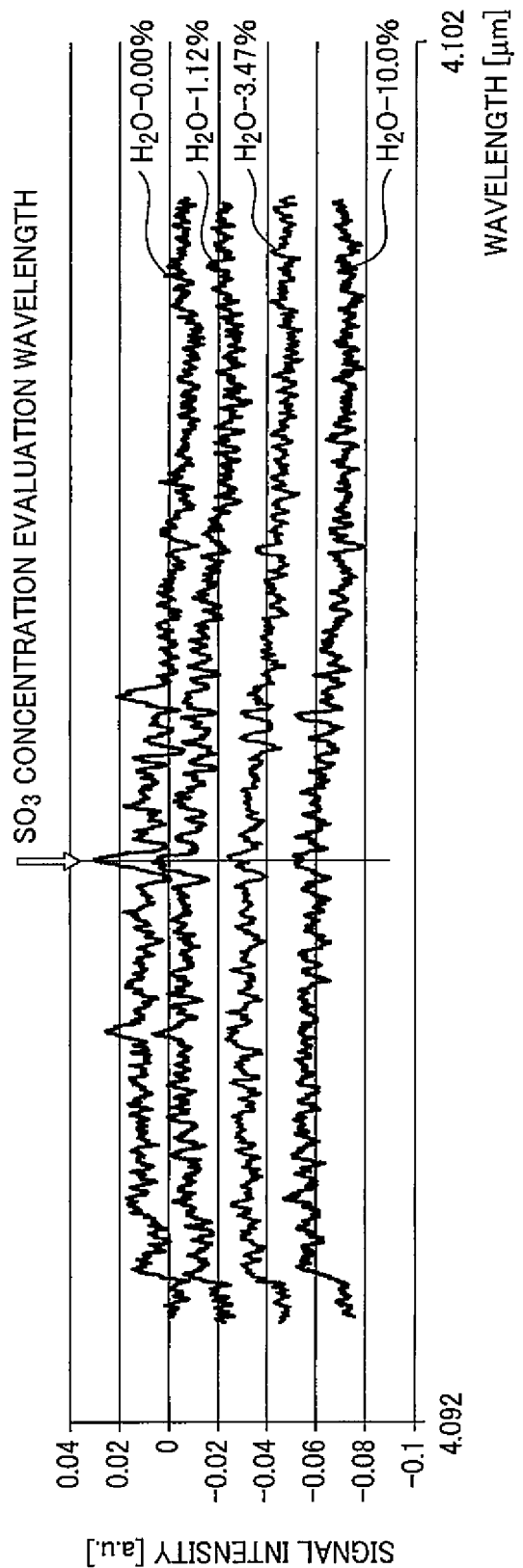
FIG. 8 is a graph illustrating the relationship between the $SO_3$ spectrum and the amount of $H_2O$ in the gas.

Then, the spectrum of $SO_3$ was measured in each $H_2O$ concentration condition, and a group of spectra illustrated in FIG. 8 were obtained.

Next, the concentration of $SO_3$ under each $H_2O$ concentration condition was calculated from the peak intensity of the absorption spectrum of $SO_3$ ($SO_3$ concentration evaluation wavelength) illustrated in FIG. 8. Meanwhile, the equilibrium concentration of $SO_3$ was calculated from each $H_2O$ concentration condition, and the temperature (290° C.) and the pressure (1 atmospheric pressure) of the flue gas, which are shown in Non-Patent Document 3.

Figure 9:
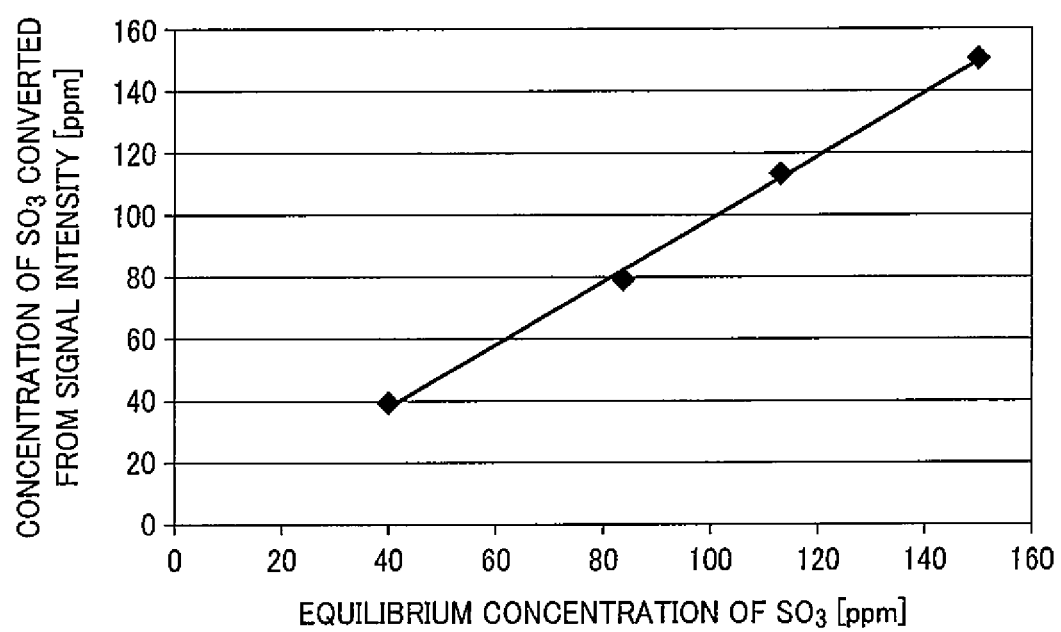
FIG. 9 is a graph illustrating the relationship between the equilibrium concentration of $SO_3$ and the concentration of $SO_3$ converted from a signal intensity.

After the above calculation, the concentrations of $SO_3$ converted from the peak intensities of $SO_3$ measured in this example were compared with the equilibrium concentrations of $SO_3$ calculated based on Non-Patent Document 3, and the comparison result is illustrated in FIG. 9. As is apparent from FIG. 9, both agree in all $H_2O$ concentration conditions. From this result, it was confirmed that the equilibrium state of $SO_3/H_2O/H_2SO_4$ shown in Non-Patent Document 3 is valid.

From the result above, it became apparent that using the $SO_3$ analysis device 10A according to this example makes it possible to measure in-situ (directly measure), for example, the concentration of $SO_3$, the concentration of $H_2SO_4$, and the total concentration of $SO_3$ (the total sum of the concentration of $SO_3$ and the concentration of $H_2SO_4$) in the flue gas 1 containing a large amount of $H_2O$, such as actual combustion flue gases, which had been conventionally impossible.

Note that since the conventional sampling measurement was made at one point, concentration measurement at multiple points was necessary to obtain a true representative value of the concentration of $SO_3$ in a furnace. On the other hand, since the concentration of $SO_3$ is measured with the laser light 2 crossing the inside of the flue in this example, the measurement result shows the average of the optical path, which means a true representative value of the concentration of $SO_3$ in the furnace can be measured in-situ.

Note that the $SO_3$ analysis device 10A may be disposed, for example, to a flue at an exit of a furnace of a combustion plant that burns heavy oil, through which flue gas at 300 to 500° C. flows. This is because that even if the temperature of the flue gas to be measured is within the above temperature range, the $SO_3$ analysis device 10A can measure the concentration of $SO_3$ in the flue gas promptly, and that based on the measurement result, the combustion plant that burns heavy oil can be operated more efficiently. In addition, the $SO_3$ analysis device 10A can be disposed to a flue through which flue gas at 500° C. or higher flows, where $H_2O$ and $SO_3$ can exist completely independently (where $H_2SO_4$ is not generated).

EXAMPLE 2

Descriptions will be provided for an $SO_3$ analysis device according to a second embodiment of the present invention using FIGS. 10 to 13.

Figure 10:
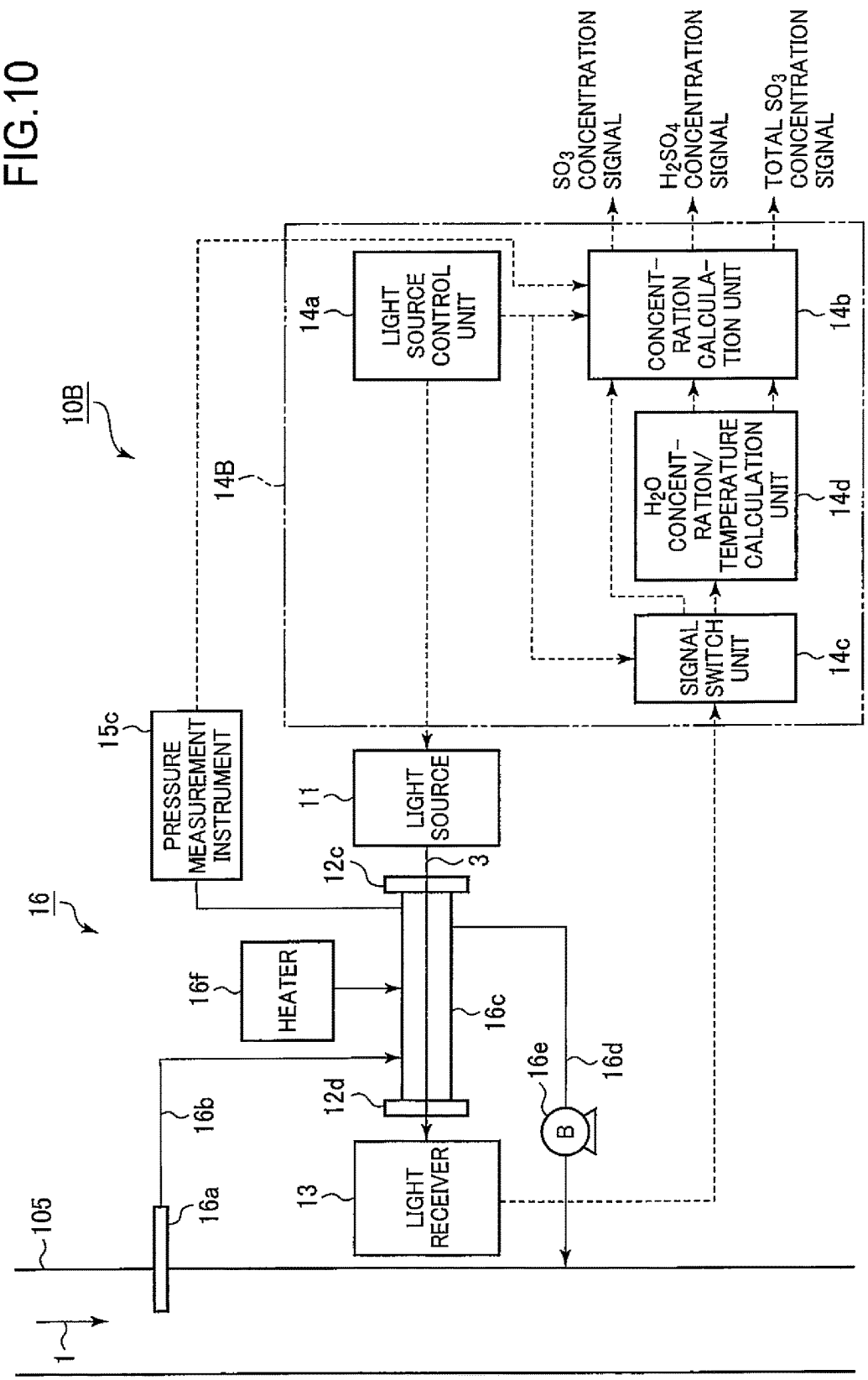
FIG. 10 is a schematic configuration diagram of an $SO_3$ analysis device according to a second example of the present invention.

As illustrated in FIG. 10, an $SO_3$ analysis device 10B according to this example includes the same equipment as that in the $SO_3$ analysis device 10A according to the first example, and also includes a sampling device 16, the pressure measurement instrument 15*c*, and a control device 14B. The sampling device 16 includes a sampling pipe 16*a*, a delivery pipe 16*b*, a sampling cell 16*c*, a discharge pipe 16*d*, and a blower 16*e*. The control device 14B includes the light source control unit 14*a*, the concentration calculation unit 14*b*, a signal switch unit 14*c*, and $H_2O$ concentration/temperature calculation unit 14*d*. The concentration calculation unit 14*b* calculates and outputs the concentration of $SO_3$, the concentration of $H_2SO_4$, and the total concentration of $SO_3$ based on the light reception signal, an $H_2O$ concentration signal, the temperature signal, the pressure signal, and the light source control reference signal which are obtained with the above equipment and the above calculation units.

The pressure measurement instrument 15*c* is disposed so as to measure the pressure inside the sampling cell 16*c*, and capable of measuring the pressure of the flue gas 1 flowing through the inside the sampling cell 16*c*. The pressure of the flue gas 1, which is the measurement result of measuring with the pressure measurement instrument 15*c*, is converted into a pressure signal, which is outputted to the concentration calculation unit 14*b* of the control device 14B.

The sampling pipe 16*a* is disposed with its distal end side protruded into the flue 105, and samples the flue gas 1 flowing through the flue 105.

The proximal end side of the delivery pipe 16*b* is connected to the proximal end side of the sampling pipe 16*a*, and the distal end side of the delivery pipe 16*b* is connected to the proximal end side of the sampling cell 16*c*.

The distal end of the sampling cell 16*c* is coupled to the light source 11 through a window 12*c*, and the proximal end of the sampling cell 16*c* is coupled to the light receiver 13 through a window 12*d*. Note that it is preferable that the windows 12*c* and 12*d* be made of, for example, sapphire in the same way as in the windows 12*a* and 12*b*.

The proximal end of the discharge pipe 16*d* is connected to the sampling cell 16*c*, and the distal end of the discharge pipe 16*d* is connected to the flue 105 downstream of the sampling pipe 16*a* in the flowing direction of the flue gas. The blower 16*e* is disposed in the middle of the discharge pipe 16*d*. With the operation of this blower 16*e*, a part of the flue gas 1 flowing through the flue 105 will be introduced through the sampling pipe 16a and the delivery pipe 16b into the sampling cell 16c, and the flue gas 1 having flowed through the sampling cell 16c will be returned through the discharge pipe 16d to the flue 105.

The sampling device 16 further includes a heater 16f that heats the sampling pipe 16a, the delivery pipe 16b, and the sampling cell 16c to keep the temperature of the internal flue gas 1 at a desired temperature higher than or equal to the acid dew point. This allows the insides of the sampling pipe 16a, the delivery pipe 16b, and the sampling cell 16c to be kept at a constant temperature, eliminating sulfuric acid mist from the flue gas 1 inside these, and makes it possible for $SO_3/H_2O/H_2SO_4$ to exist in the gaseous state.

The light source control unit 14a of the control device 14B transmits the light source control signal to the light source 11 to control the wavelength of laser light 3 emitted by the light source 11, and transmits the light source control reference signal to the concentration calculation unit 14b and the signal switch unit 14c. The light source control reference signal is a signal having the wavelength information on the laser light emitted by the light source 11 according to the light source control signal.

Here, the main operation of the above $SO_3$ analysis device 10B will be described.

First, the heater 16f is activated to heat the sampling pipe 16a, the delivery pipe 16b, and the sampling cell 16c. By doing this, the temperatures inside the sampling pipe 16a, the delivery pipe 16b, and the sampling cell 16c are kept at temperatures higher than or equal to the acid dew point.

Then, the blower 16e is activated. This will cause a part of the flue gas 1 flowing through the flue 105 to flow into the sampling cell 16c through the sampling pipe 16a and the delivery pipe 16b.

Next, the light source 11 emits the laser light 3 with predetermined wavelengths (for example, an $SO_3$ absorption wavelength in the 4.060 to 4.182 μm band and an $H_2O$ absorption wavelength near the $SO_3$ absorption wavelength (for example 4.09714 μm)) based on the light source control signal from the light source control unit 14a of the control device 14B. The laser light 3 is received by the light receiver 13 through the window 12c, the flue gas 1 inside the sampling cell 16c, and the window 12d. The light receiver 13 transmits the light reception signal corresponding to the received laser light 3, to the signal switch unit 14c of the control device 14B.

The light reception signal inputted to the signal switch unit 14c of the control device 14B is split into a light reception signal for $SO_3$ measurement and a light reception signal for $H_2O$ measurement based on the light source control reference signal transmitted from the light source control unit 14a, and the light reception signal for $SO_3$ measurement is transmitted to the concentration calculation unit 14b of the control device 14B, and the light reception signal for $H_2O$ measurement to the $H_2O$ concentration/temperature calculation unit 14d of the control device 14B.

The $H_2O$ concentration/temperature calculation unit 14d calculates the temperature as well as the concentration of $H_2O$ based on the transmitted light reception signal for $H_2O$ measurement, and transmits them as the temperature signal and the $H_2O$ concentration signal, respectively, to the concentration calculation unit 14b.

The pressure measurement instrument 15c measures the pressure inside the sampling cell 16c and transmits the pressure signal to the concentration calculation unit 14b.

The concentration calculation unit 14b calculates the concentration of $SO_3$ in the flue gas 1 by means of the infrared spectroscopy based on the pressure signal, the temperature signal, the $H_2O$ concentration signal, the light reception signal for $SO_3$ measurement, and the light source control reference signal. The concentration of $H_2SO_4$ is calculated from this concentration of $SO_3$, and the concentration of $H_2O$, the temperature, and the pressure by means of equilibrium calculation. By summing them, the total concentration of $SO_3$ (the total sum of the concentration of $SO_3$ and the concentration of $H_2SO_4$) is calculated. Each of them is outputted as a concentration signal.

Figure 11:
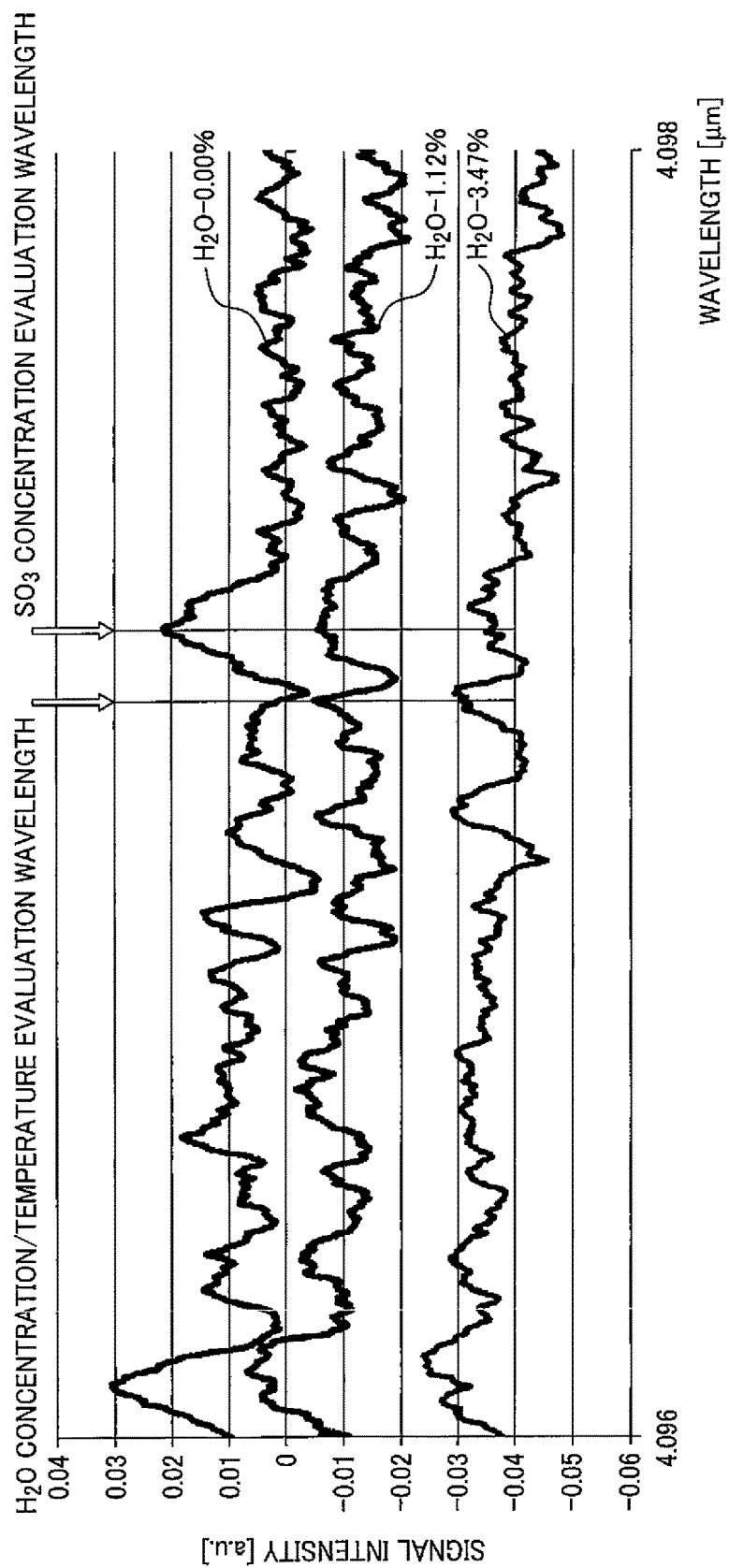
FIG. 11 is a graph illustrating a result of measuring the concentration of $SO_3$, the concentration of $H_2O$, and the temperature simultaneously with a single light source included in the $SO_3$ analysis device.
Figure 12:
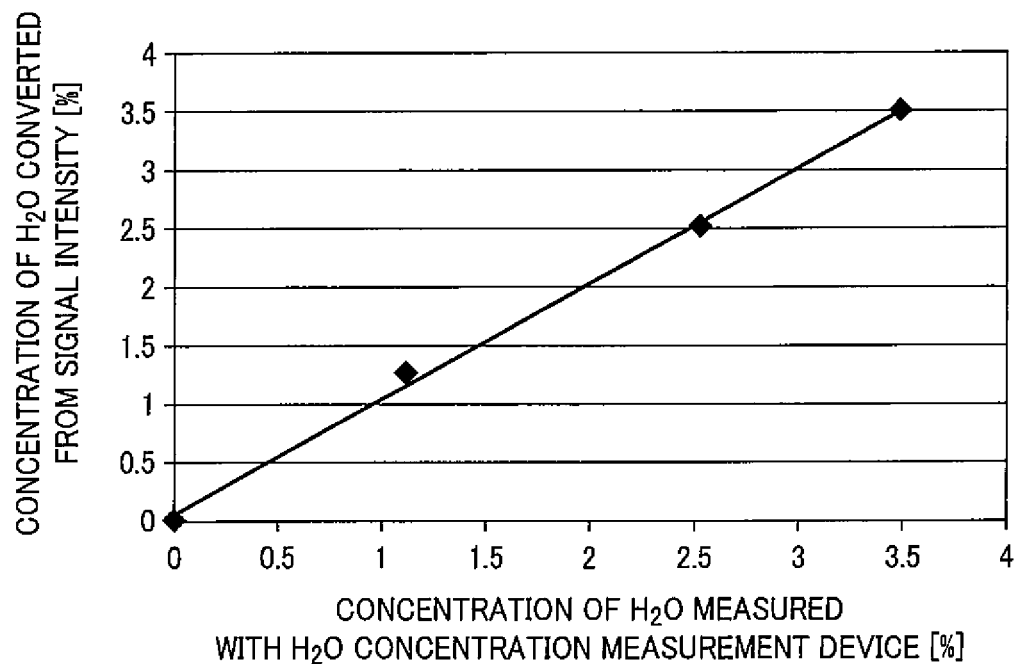
FIG. 12 is a graph illustrating the relationship between the concentration of $H_2O$ measured with a conventional $H_2O$ concentration measurement device and the concentration of $H_2O$ converted from the signal intensity.
Figure 13:
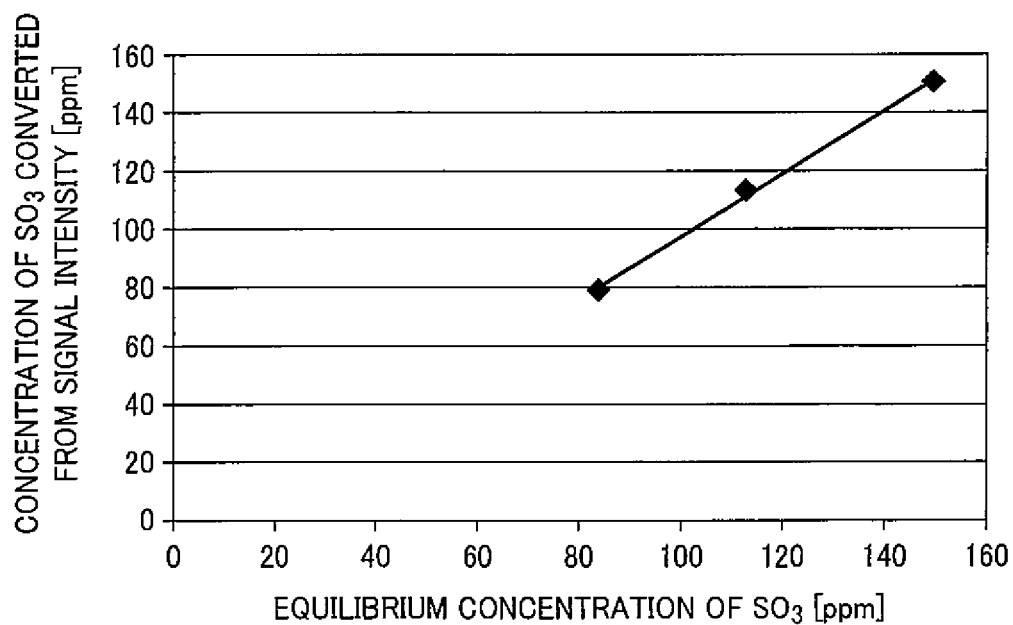
FIG. 13 is a graph illustrating the relationship between the equilibrium concentrations of $SO_3$ and the concentration of $SO_3$ converted from the signal intensity.

Specifically, as illustrated in FIG. 11, the peak of the $SO_3$ spectrum reduces along with the concentration of $H_2O$ (changed to $H_2SO_4$ in the chemical reaction), and the peak of the $H_2O$ spectrum increases along with the concentration of $H_2O$. At that time, it was confirmed as illustrated in FIG. 12 that the concentration of $H_2O$ measured with a conventional $H_2O$ concentration analysis device and the concentration of $H_2O$ calculated from the peak intensity of the $H_2O$ spectrum (converted from the signal intensity) agrees to each other. Note that the temperature of the atmosphere can be calculated, for example, from the peak shape or the like of the $H_2O$ spectrum as shown in Patent Document 1 and is used for correction when the concentration of $H_2O$ and the concentration of $SO_3$ are calculated. In addition, the concentration of $SO_3$ when $H_2O$ is mixed agrees to the equilibrium concentration of $SO_3$ calculated from the $H_2O$ concentration and the temperature. From this, it can be judged that $SO_3$, $H_2O$, and $H_2SO_4$ have reached equilibrium, and as a result, the concentration of $H_2SO_4$ in this state can be calculated.

Thus, even in the case where the flue gas 1 is sampled, the $SO_3$ analysis device 10B according to this example including the above equipment makes it possible to measure the concentration of $SO_3$, the concentration of $H_2SO_4$, and the total concentration of $SO_3$ (the total sum of the concentration of $SO_3$ and the concentration of $H_2SO_4$) in the flue gas 1 promptly and accurately without removing coexisting gases other than $SO_3$ and dust in the flue gas 1.

Moreover, it is possible to provide the $SO_3$ analysis device 10B without a large-scale modification work such as attaching measurement windows to a furnace in which gas flows.

Note that the $SO_3$ analysis device 10B described above can be provided, for example, to a flue downstream of a combustion plant that burns heavy oil in which flue gas at a room temperature to 300° C. flows. This is because when the temperature of the flue gas to be measured is within the above temperature range, the concentration of $SO_3$ in the flue gas can be measured promptly with the $SO_3$ analysis device 10B, and based on this measurement result, the combustion plant that burns heavy oil can be operated more efficiently.

INDUSTRIAL APPLICABILITY

Since the $SO_3$ analysis method and analysis device according to the present invention can measure the concentration of $SO_3$ and the total $SO_3$ molecule concentration in flue gas accurately and promptly without pretreatment such as removing dust and humidity, for various kinds of combustion equipment that generate $SO_3$ such as a combustion plant that burns heavy oil, it can be utilized extremely usefully in industrial applications.

REFERENCE SIGNS LIST 1 flue gas
2, 3 laser light 10A, 10B SO₃ analysis device
11 light source (light emission means)
12a to 12d window plate portion
13 light receiver (light reception means)
14, 14B control device
14a light source control unit (wavelength control means)
14b concentration calculation unit (SO₃ concentration calculation means, H₂SO₄ concentration calculation means)
14c signal switch unit
14d H₂O concentration/temperature calculation unit (H₂O concentration calculation means, temperature calculation means)
15a water concentration measurement instrument (H₂O concentration measurement means)
15b temperature measurement instrument (temperature measurement means)
15c pressure measurement instrument (pressure measurement means)
16 sampling device
16f heater (heating means)

The invention claimed is:

1. An SO₃ analysis device comprising:
light emission means for emitting laser light to gas containing SO₃, CO₂, and H₂O;
light reception means for receiving the laser light that has been emitted to the gas and has passed through the gas;
wavelength control means for performing control such that a wavelength of the laser light emitted by the light emission means is at an absorption wavelength of SO₃ in a 4.060 to 4.182 μm band;
SO₃ concentration calculation means for calculating a concentration of SO₃ by means of infrared spectroscopy based on an output from the light reception means and a reference signal from the wavelength control means;
H₂O concentration measurement means for measuring a concentration of H₂O in the gas; and
H₂SO₄ concentration calculation means for calculating a concentration of H₂SO₄ by means of equilibrium calculation using the concentration of SO₃ calculated by the SO₃ concentration calculation means and the concentration of H₂O measured by the H₂O concentration measurement means.

2. The SO₃ analysis device according to claim 1, wherein the wavelength control means performs control such that the wavelength of the laser light is 4.093 to 4.098 μm, 4.1045 to 4.1065 μm, 4.110 to 4.115 μm, 4.117 to 4.126 μm, or 4.131 to 4.132 μm.

3. The SO₃ analysis device according to claim 1, wherein the light emission means includes nonlinear optical crystal, generates, by means of difference frequency generation using inputs of laser light with a wavelength of $\lambda_1$ and laser light of a wavelength of $\lambda_2$, laser light with a wavelength of $\lambda_3$ satisfying $1/\lambda_3 = 1/\lambda_1 - 1/\lambda_2$, and outputs the laser light with the wavelength of $\lambda_3$.

4. The SO₃ analysis device according to claim 1, further comprising
temperature measurement means for measuring a temperature of the gas, wherein
the SO₃ concentration calculation means calculates the concentration of SO₃ by means of the infrared spectroscopy, using also the temperature of the gas measured by the temperature measurement means.

5. The SO₃ analysis device according to claim 1, further comprising
pressure measurement means for measuring a pressure of the gas, wherein
the SO₃ concentration calculation means calculates the concentration of SO₃ by means of the infrared spectroscopy, using also the pressure of the gas measured by the pressure measurement means.

6. The SO₃ analysis device according to claim 1, further comprising
sampling means for sampling the gas, wherein
the light emission means emits the laser light to the gas sampled by the sampling means.

7. The SO₃ analysis device according to claim 6, further comprising
heating means for heating the gas sampled by the sampling means.

8. An SO₃ analysis method comprising:
emitting, by light emission means, laser light to gas containing SO₃, CO₂, and H₂O, the laser light having a wavelength controlled at 4.060 to 4.182 μm by wavelength control means;
receiving, by light reception means, the laser light emitted to the gas;
calculating a concentration of SO₃ by means of infrared spectroscopy based on an output from the light reception means and a reference signal from the wavelength control means;
measuring a concentration of H₂O in the gas; and
calculating a concentration of H₂SO₄ by means of equilibrium calculation using the concentration of SO₃ and the concentration of H₂O.

* * * * *